United States Patent [19]
Hsieh

[11] Patent Number: 5,313,969
[45] Date of Patent: May 24, 1994

[54] INSTANT PRESSURE-REDUCING PROCESS AND DEVICE FOR A BLOOD-GATHERING TUBE

[76] Inventor: Ch'ing-Lung Hsieh, 6F-3, No. 20, Wu-Chyuan-Er Rd., Shin Juang City, Taipei County, Taiwan

[21] Appl. No.: 987,175
[22] Filed: Dec. 8, 1992
[51] Int. Cl.$^5$ .................................................. A61B 5/00
[52] U.S. Cl. .................................... 128/764; 141/65
[58] Field of Search ................. 128/763, 764, 770, 760

[56] References Cited

U.S. PATENT DOCUMENTS 4,063,460 12/1977 Svensson .............................. 141/65
4,327,746 5/1982 Feaster ................................ 128/764

FOREIGN PATENT DOCUMENTS 7222395 1/1985 Taiwan .

Primary Examiner—Max Hindenburg
Attorney, Agent, or Firm—Jacobson, Price, Holman & Stern

[57] ABSTRACT

The present invention relates to an instant pressure-reducing process and device for a blood-gathering tube which comprises a blood-gathering tube in a state of normal pressure and a pressure reducing device, wherein the blood-gathering tube in a state of normal pressure comprises a tube body made of plastic or other cheap material and an elastic cork. One end of the tube body is an opening and another end is closed. The central part of elastic cork is thinner in favor of being pierced through by the injection needle head, the elastic cork is tightly nested into the opening of tube body under normal pressure so as to separate inside of the tube body from outside. The pressure-reducing device comprises an injection needle head and a pressure-reducing transformer at least. The needle head is nested into the pressure-reducing transformer.

12 Claims, 11 Drawing Sheets

FIG. 4
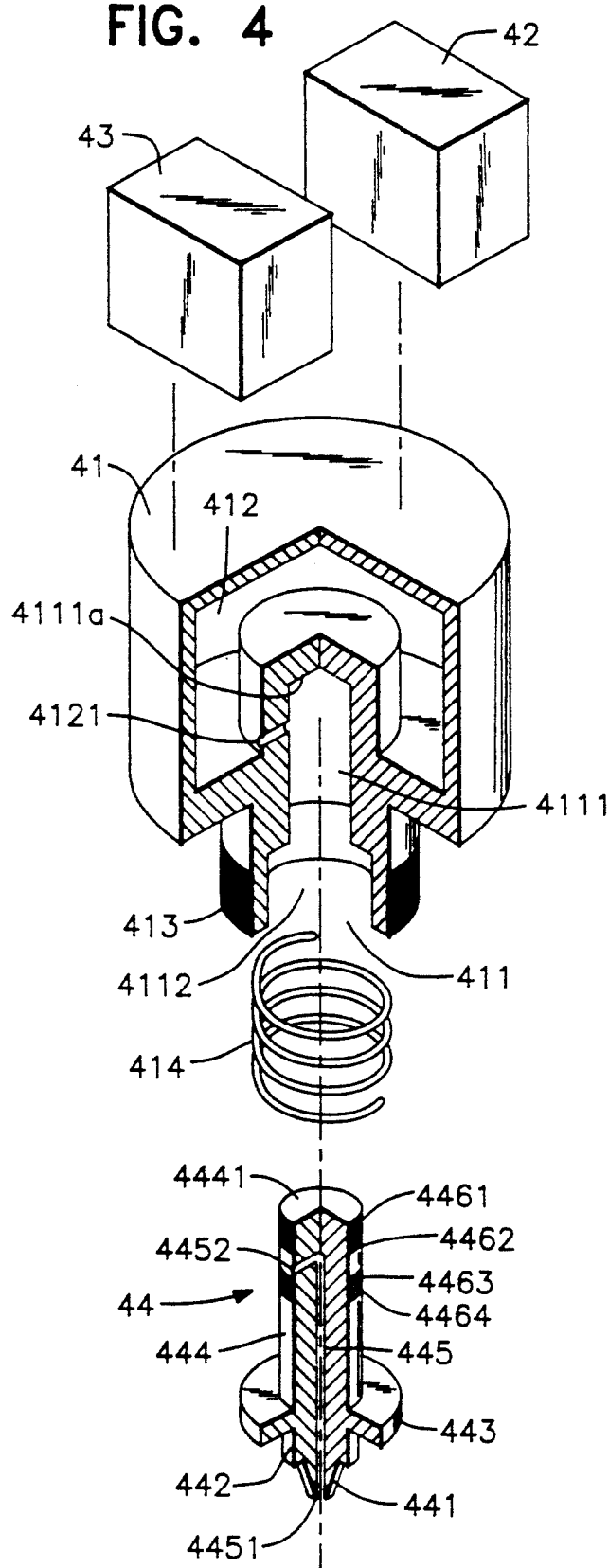
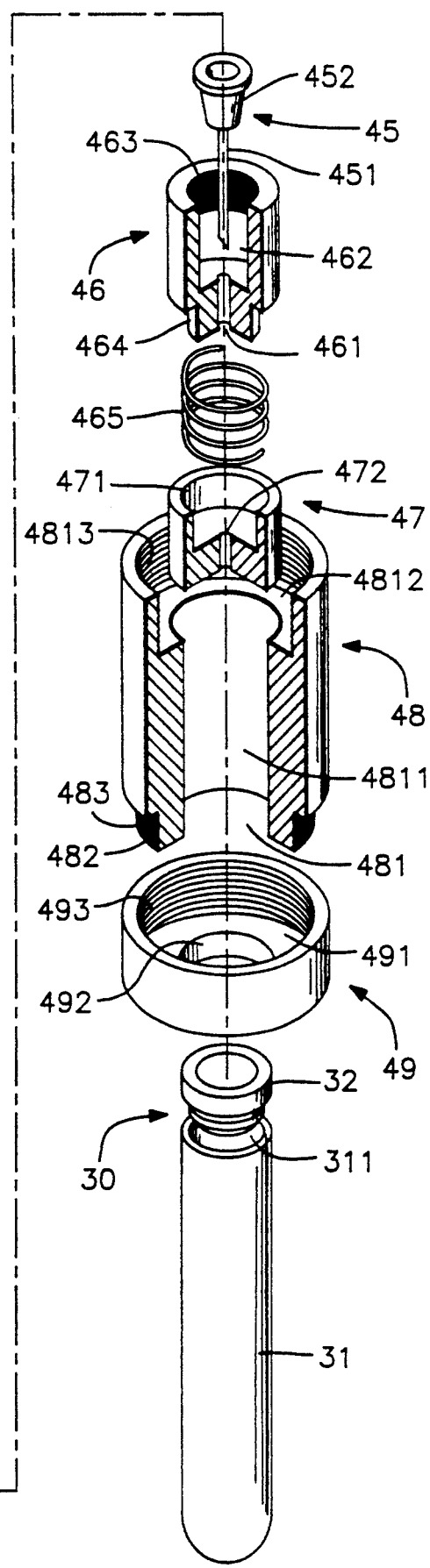

5,313,969

INSTANT PRESSURE-REDUCING PROCESS AND DEVICE FOR A BLOOD-GATHERING TUBE

The present invention relates to an instant pressure-reducing process and device for a blood-gathering tube, in particular an instant pressure-reducing of the blood-gathering tube in a state of non-vacuum and normal pressure to form a state of vacuum for proceeding with blood-gathering before starting blood-gathering so as to offer an instant pressure-reducing process and device for a blood-gathering tube of being convenient, effective and low-cost without maintaining the blood-gathering tube in a state of enough low-pressure (i.e. vacuum) for a long time.

BACKGROUND OF THE INVENTION

While proceeding biochemical experiments at normal hospitals in the earlier times, a syringe tube in general is always used for blood-gathering of a human body, then filling the blood from the syringe tube into a test tube (i.e. the blood-gathering tube) in order to proceed with the examinations or biochemical experiments. In this course, except each syringe tube and test tube for use, the blood of human body has to be filled into the test tube through the syringe tube, so the probability of blood pollution and operating cost of the medical personnel are increased.

The blood-gathering device disclosed in Taiwan Utility Model Patent No. 25838 (Application No. 7222395) consists of a needle holder, a syringe tube, a piston and puller, making use of pulling motion of the puller and piston for blood-gathering. When blood-gathering is finished, the puller is removed through turning it counterclockwise. After removing its injection needle head, a cover is screwed onto the needle holder so that the syringe tube becomes a test tube for storing the blood. Because its structure is in need of such elements as a piston, a puller, etc., it is difficult to lower its cost. After blood-gathering is finished, the puller has to be removed with a specific process and a cover has to be screwed onto the needle holder, such a follow-up process will increase the working burden of medical personnel.

In view of the above, some manufacturers have developed a vacuum blood-gathering tube 10 as shown in FIG. 1 in matching with an injection needle jacket 20 as shown in FIG. 2 for blood-gathering. As shown in FIG. 1, the vacuum blood-gathering tube 10 comprises a tube body 11 and an elastic cork 12. The tube body 11 is normally made of glass or transparent resin with better air-tight property. However, the tube body made of resin remains poorer than glass in the aspect of air-tightness and is rather difficult to keep the condition of long-term vacuum, and tends to breach and is detrimental to shipping and storage. One end of the tube body 11 is closed and another end is an opening. The elastic cork 12 is normally made of synthetic rubber. So far as the vacuum blood-gathering tube 10 is concerned, the elastic cork is tightly nested in the opening of tube body 11 in a vacuum low-pressure environment so as to maintain a condition of vacuum low-pressure in the tube body 11.

As shown in FIG. 2, the injection needle jacket 20 comprises a sleeve 21 and a needle head 22. One end of the sleeve 21 is provided with a threaded hole 211 and another end is an opening 212. The outer edge in the middle section of needle head 22 is provided with a thread 221. Two ends 222 and 223 of the needle head 22 are shaped as sharp, and the thread 221 in the middle section of needle head 22 is screwed into the threaded hole 211 of sleeve 21 so that one end 222 of the needle head 22 is outside the threaded hole 211 of sleeve 21 for thrusting into the blood vessel of a human body, and another end 223 is on the inner edge of sleeve 21 and able to pierce through the elastic cork 12 of vacuum blood-gathering tube 10.

When blood-gathering, to thrust one end 222 of needle head 22 of injection needle jacket 20 into the blood vessel of human body, then to nest the vacuum blood-gathering tube 10 into the sleeve 21 of injection needle jacket 20, another end 223 of the needle head 22 in the sleeve 21 pierces through the elastic cork 12 of vacuum blood-gathering tube 10 and enters into the tube body 11 in a state of vacuum low-pressure, making use of low pressure in the tube body 11 attracts blood of human body to flow into the tube body 11. After blood-gathering is finished, to remove the vacuum blood-gathering tube 10 from the injection needle jacket 20. Since the needle hole wall formed on the elastic cork 12 by thrusting the needle head 22 into the vacuum blood-gathering tube 10 can stretch and restore its closed state at once to release pressure from it after the needle head 22 disengages from the elastic cork 12, the blood in the vacuum blood-gathering tube 10 will never be polluted or exude out from the needle hole.

The vacuum blood-gathering tube 10 tightly nested at the opening of tube body 11 and made of glass or transparent resin in a low-pressure environment as shown in Fig. 1 will not be fully air-tight and usable because it is stored for a long time (even up to 2-3 years) or the elastic cork 12 is not tightly nested into the tube body 11. Therefore, almost all of the manufacturers use the glass tube body with better air-tightness waive the cheaper tube body made of transparent resin or other plastic materials. The air-tightness of tube body made of glass is better but tends to breach because of a slight collision during shipping or storage and is possible to leak air for its long storage time or inadequate air-tightness of nesting the elastic cork into the tube body.

SUMMARY OF THE INVENTION

In view of the above, the present invention offers an instant pressure-reducing process and device for a blood-gathering tube which can instantly pressure-reduce the blood-gathering tube in a state of normal pressure to form a vacuum tube before proceeding with blood-gathering which comprises a blood-gathering tube in a state of normal pressure and a pressure-reducing device, wherein the blood-gathering tube in a state of normal pressure comprises a tube body made of plastic or other cheap material and an elastic cork. One end of the tube body is an opening and another end is closed. The central part of elastic cork is thinner in favor of being pierced through by the injection needle head, the elastic cork is tightly nested into the opening of tube body under normal pressure so as to separate inside of the tube body from outside. The pressure-reducing device comprises an injection needle head and a pressure-reducing transformer at least. The needle head is nested into the pressure-reducing transformer and used to pierce through the elastic cork of blood-gathering tube nested in the opening of tube body for exhausting the air in the tube body and instantly pressure-reducing the interior of tube body to form a vacuum in favor of blood-gathering.

The object of the present invention is to offer an instant pressure-reducing process and device for a blood-gathering tube which need not maintain the condition of enough low pressure (i.e. vacuum) in the blood-gathering tube for a long term.

Another object of the present invention is to offer an instant pressure-reducing process and device for a blood-gathering tube, wherein the blood-gathering tube can be instantly pressure-reduced to form a vacuum when blood-gathering.

More another object of the present invention is to offer an instant pressure-reducing process and device for a blood-gathering tube, wherein the tube body of blood-gathering tube is made of plastic or other cheap material.

Further another object of the present invention is to offer an instant pressure-reducing process and device for a blood-gathering tube which is provided with a pressure-reducing device of the injection needle head, and the needle head is used to pierce through the elastic cork nested in the opening of blood-gathering tube for instantly exhausting the air in the tube body and instantly pressure-reducing the interior of tube body to form a vacuum.

The other object of the present invention is to offer an instant pressure-reducing process and device for a blood-gathering tube, comprising an injection needle head and a pressure-reducing transformer so as to instantly pressure-reduce the blood-gathering tube with normal pressure to form a vacuum.

BRIEF DESCRIPTION OF THE DRAWINGS

FIG. 4 shows a breakdown view of the first embodiment of the present invention, in the form of a blood-gathering tube and the pressure-reducing device.

DETAILED DESCRIPTION OF THE INVENTION

The present invention is described in detail in matching with the embodiments and accompanying drawings.

First Embodiment

Figure 1:
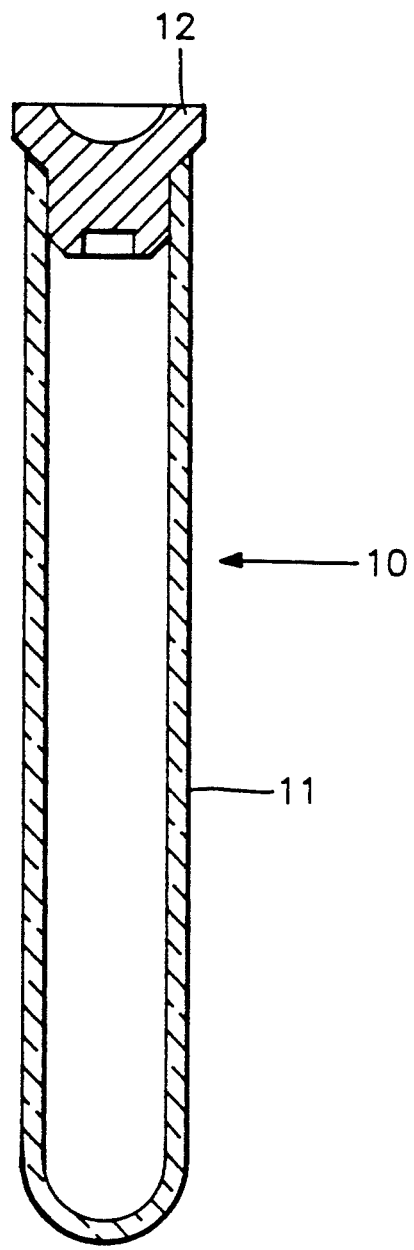
FIG. 1 shows a section view of a conventional vacuum blood-gathering tube.
Figure 2:
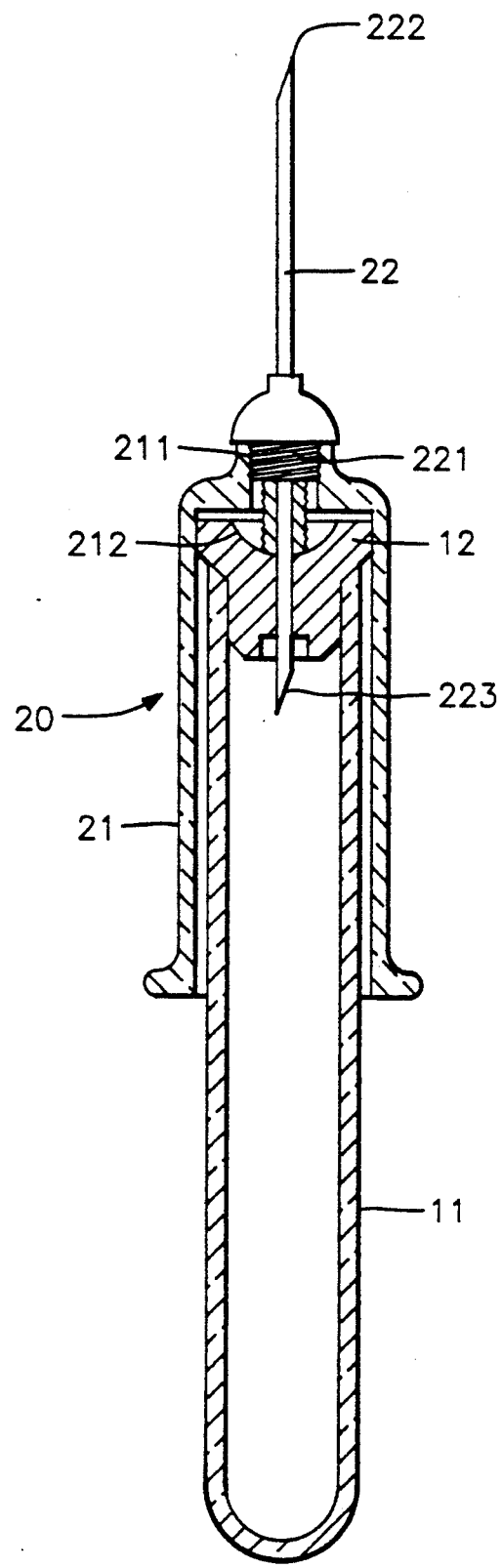
FIG. 2 shows a schematic view of a conventional vacuum blood-gathering tube in matching with an injection needle jacket.
Figure 3:
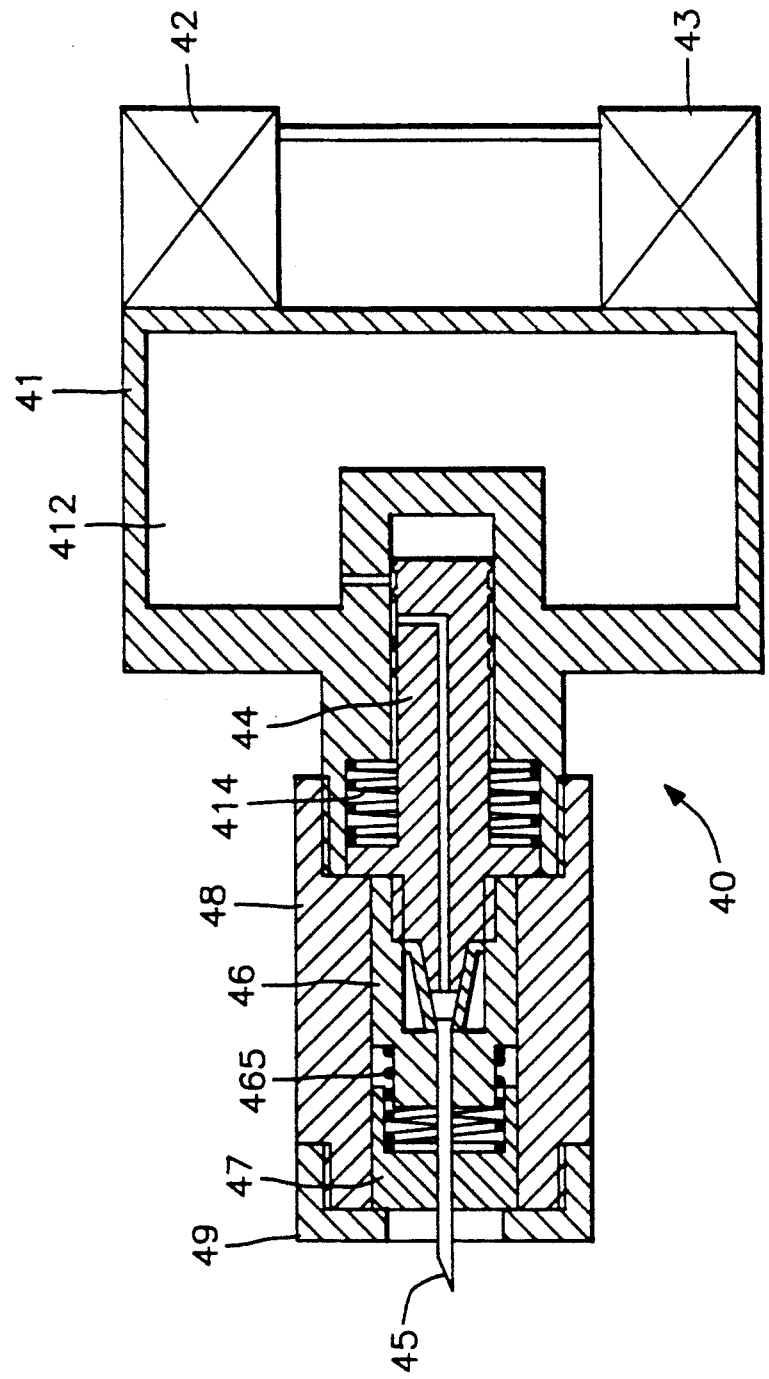
FIG. 3 shows a section view of a first embodiment of the present invention, in the form of a pressure-reducing device.
Figure 5:
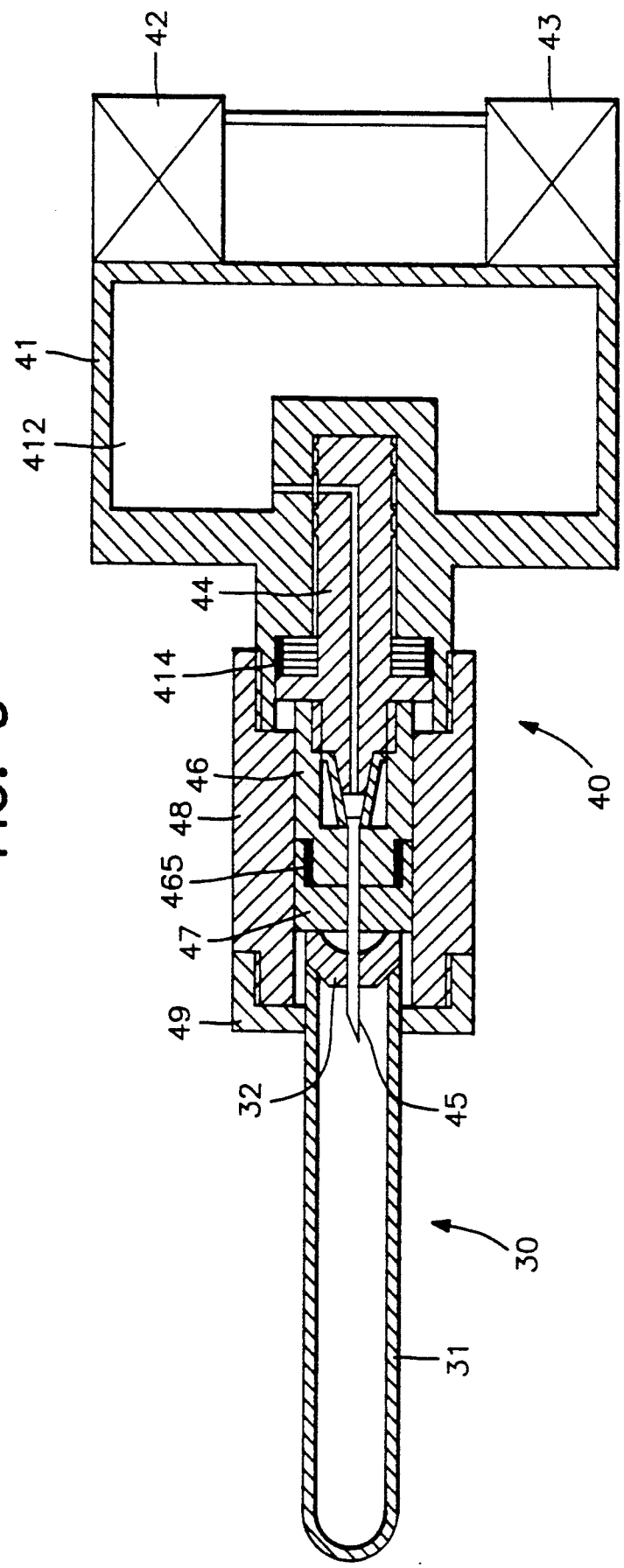
FIG. 5 shows a section view of the first embodiment of the present invention in proceeding with pressure-reducing by a blood-gathering tube piercing into the pressure-reducing device.

As shown in FIG. 3 to 5, the present invention comprises a blood-gathering tube 30 in a state of normal pressure and a pressure-reducing device 40, wherein the blood-gathering tube 30 comprises a tube body 31 and an elastic cork 32. One end of the tube body 31 is an opening 311 and another end is closed. The tube body 31 is made of cheap plastic. The elastic cork 32 is made of rubber, the central part of elastic cork 32 is thinner in favor of being pierced through by a needle head. As shown in FIG. 4 and 5, the elastic cork 32 is tightly nested into the opening 311 of tube body 31 under normal pressure so as to separate the inside from outside of tube body 31.

As shown in FIG. 3 and 4, the pressure-reducing device 40 consists of a vacuum body 41 with a pressure switch 42 and a vacuum pump 43, a sliding socket pipe 44, a needle head 45, a needle jacket 46, a sliding sleeve 47, a needle head casing 48 and a sliding sleeve cover 49, wherein a T-shaped groove 411 and a vacuum chamber 412 are provided in the vacuum body 41. The vacuum chamber 412 is connected to a pressure switch 42 and a vacuum pump 43. The pressure switch 42 is used to control the vacuum pump 43 so as to keep the vacuum chamber 412 always in a state of low pressure (i.e. a vacuum). The T-shaped groove 411 consists of a lateral groove 4111 connecting to a longitudinal groove 4112. An air pipe 4121 is provided between the inner edge of the lateral groove 4111 and vacuum chamber 412. The air pipe 4121 is connected to the vacuum chamber 412. The longitudinal groove 4112 is wider than the lateral groove 4111. The outer edge of housing of longitudinal groove 4112 is provided with a plurality of threads 413. The inner edge of longitudinal groove 4112 is provided with an annular spring 414.

The front end of sliding socket pipe 44 is provided with a conical needle seat 441, the rear of needle seat 441 is provided with a plurality of threads 442, the rear of threads 442 is provided with a protruding annulation 443, the shape of protruding annulation 443 is mutually corresponding to the shape of inner edge of longitudinal groove 4112 of vacuum body 41 The width of protruding annulation 443 is slightly smaller than the width of longitudinal groove 4112. A pipe body 444 is extended from the rear of protruding annulation 443. A L-shaped air groove 445 is provided in the sliding socket pipe 44. An opening 4451 of the air groove 445 is provided at the end of needle seat 441. Another opening 4452 of the air groove 445 is provided at one side of the pipe body 444. The pipe body 444 on the front and rear sides of opening 4452 is respectively provided with sealing annulations 4461, 4462, 4463 and 4464. The shape and size of outer edge of sealing annulations 4461, 4462, 4463 and 4464 are the same as those of inner edge of lateral groove 4111 of vacuum body 41. The opening 4452 of air groove 445 of sliding socket pipe 44 is provided at one side of the pipe body 444. The distance between the opening 4452 and protruding annulation 443 is slightly larger than the distance between the air pipe 4121 on the inner edge of lateral groove 4111 of vacuum body 41 and longitudinal groove 4112. The distance between the air pipe 4121 of vacuum body 41 and the side wall 4111a of lateral groove 4111 is approximately equal to the distance between the opening 4452 of air groove 445 of sliding socket pipe 44 and the end of pipe body 444. When the end 4441 of pipe body 444 of sliding socket pipe 44 extends into the lateral groove 4111 of vacuum body 41 and contacts the side wall of lateral groove 4111, the opening 4452 of air groove 445 of sliding socket pipe 44 is connected to the air pipe 4121 on the inner edge of lateral groove 4111 of vacuum body 41.

The needle head 45 consists of a sharp hollow needle body 451 and a seat sleeve 452 and is a conventional article. The seat sleeve 452 can be easily nested into the needle seat 441 of sliding socket pipe 44.

A needle head pipe 461 with a shape corresponding to the shape of needle head 45 is provided to the inner edge of needle jacket 46. The rear section of needle head pipe 461 is suitably extended to form a seat sleeve cover 462 which can be nested onto the outer edge of seat sleeve 452 of needle head 45. The inner edge of seat sleeve cover 462 is provided with a plurality of threads 463. The outer edge in the front section of needle jacket 46 is reduced inward to form a neck 464. The outer edge of neck 464 can be nested with an annular spring 465.

One end of the sliding sleeve 47 is provided with a recess 471. The center of recess 471 is provided with a needle groove 472 across two ends of the sliding sleeve 47. The recess 471 of sliding sleeve 47 can be just nested onto the outer edge of neck 464 of needle jacket 46. The annular spring 465 is provided between the neck 464 of needle jacket 46 and the recess 471 of sliding sleeve 47.

A T-shaped groove 481 across the front and rear ends of needle head casing 48 is provided at the inner edge of needle head casing 48. The inner diameter of lateral groove 4811 of T-shaped groove 481 is slightly smaller than the outer diameter of protruding annulation 443 of sliding socket pipe 44. The inner diameter of lateral groove 4811 is equal to or slightly larger than the outer diameter of sliding sleeve 47. The outer diameter of protruding annulation 443 is slightly smaller than the inner diameter of longitudinal groove 4812 of T-shaped groove 481. The inner edge of longitudinal groove 4812 is provided with a plurality of threads 4813 which are corresponding to the threads 413 on the outer edge of housing of longitudinal groove 4112 of vacuum body 41 and can be screwed with each other. The outer edge of front section of needle head casing 48 is reduced inward to form a neck 482. The outer edge of neck 482 is provided with a plurality of threads 483.

One side of the sliding sleeve cover 49 is provided with a recess 491. The inner diameter of recess 491 is equal to or slightly larger than the outer diameter of sliding sleeve 47. A hole 492 is provided to the center of recess 491. The inner diameter of hole 492 is slightly smaller than the outer diameter of sliding sleeve 47. The size of inner edge of hole 492 is equal to or slightly larger than the diameter of tube body 31 of blood-gathering tube 30. The inner edge of recess 491 of sliding sleeve cover 49 is provided with a plurality of threads 493 which are corresponding to the threads 483 on the outer edge of neck 482 of needle head casing 48 and can be screwed with each other.

When assembly, as shown in the drawings, the seat sleeve 452 of needle head 45 is nested onto the needle seat 441 of sliding socket pipe 44. The pipe body 444 and protruding annulation 443 of sliding socket pipe 44 are installed into the T-shaped groove 411 of vacuum body 41. The inner side of protruding annulation 443 of sliding socket pipe 44 is nested with the annular spring 414. The hollow needle body 451 of needle head 45 passes through the needle head pipe 461 of needle jacket 46. The seat sleeve cover 462 of needle jacket 46 is screwed onto the threads 442 of sliding socket pipe 44. The outer edge of neck 464 of needle jacket 46 is provided with an annular spring 465. The neck 464 of needle jacket 46 and the annular spring 465 are nested into the recess 471 of sliding sleeve 47. The hollow needle body 451 of needle head 45 passes through the needle head pipe 461 of needle jacket 46 and enters into the needle groove 472 of sliding sleeve 47.

Whem a force presses the sliding sleeve 47 to compress the annular spring 465 between the recess 471 of sliding sleeve 47 and the neck 464 of needle jacket 46, the sliding sleeve 47 moves toward the needle jacket 46 and the hollow needle body 451 of needle head 45 extends out of the needle groove 472 of sliding sleeve 47. When the force disappears, the annular spring 465 is released from the pressure and extends to let the sliding sleeve 47 move toward the sliding sleeve cover 49 and the hollow needle body 451 of needle head 45 moves into the needle groove 472 of sliding sleeve 47. The threads 4813 of longitudinal groove 4812 of needle head casing 48 are screwed with the threads 413 on the outer edge of housing of longitudinal groove 4112 of vacuum body 41 to confine the sliding socket pipe 44 in the T-shaped groove 411 of vacuum body 41. The threads 493 on the inner edge of recess 491 of sliding cover 49 are screwed with the threads 483 of neck 482 of needle head casing 48 to confine the sliding sleeve 47 in the needle head casing 48. By means of the pressure and release of the force, the annular spring 465 can compress and extend to let the sliding sleeve 47 and needle jacket 46 form a relative motion.

Before blood-gathering, as shown in FIG. 5, the interior of tube body 31 of blood-gathering tube 30 in a state of normal pressure is pressure-reduced to be a vacuum in advance and the process is described as follows:

1. First to align the opening 311 of elastic cork 32 nested on the tube body 31 of blood-gathering tube 30 with the hole 492 of sliding sleeve cover 49 of pressure-reducing device and slightly apply a pressure to push the tube body 31 forward; when the elastic cork 32 contacts the sliding sleeve 47 to compress the annular spring 465 between the recess 471 of sliding sleeve 47 and the neck 464 of needle jacket 46, the sliding sleeve 47 moves toward the needle jacket 46. Meanwhile, the share point of hollow needle body 451 in the needle groove 472 of sliding sleeve 47 pierces through the center of elastic cork 32 of blood-gathering tube 30 into the tube body 31.

2. The pressure of blood-gathering tube 30 applied to the sliding sleeve 47 compresses the annular spring 414 between the protruding annulation 443 of sliding socket pipe 44 and the longitudinal groove 4112 of vacuum body 41 through the annular spring 465, the needle jacket 46 and sliding socket pipe 44, so the pipe body 444 of sliding socket pipe 44 moves toward the inside of lateral groove 4111 of vacuum body 41, the end 4441 of pipe body 444 of sliding socket pipe 44 contacts the side wall 4111a of lateral groove 4111 of vacuum body 41, and the opening 4452 of air groove 445 of sliding socket pipe 44 communicates with the air pipe 4121 of vacuum body 41.

3. The air in the tube body 31 of blood-gathering tube 30 is quickly exhaled through the passage of air pipe 4121, the air groove 445 of sliding socket pipe 44 and the needle head 45 by making use of the low pressure (i.e. vacuum) in the vacuum chamber 412 of vacuum body 41, so the interior of tube body 31 is instantly pressure-reduced to be in a state of vacuum, then the blood-gathering tube 30 can be removed from the hole 492 of sliding sleeve cover 49 of pressure-reducing device 40 for proceeding with blood-gathering.

Second Embodiment

Figure 6:
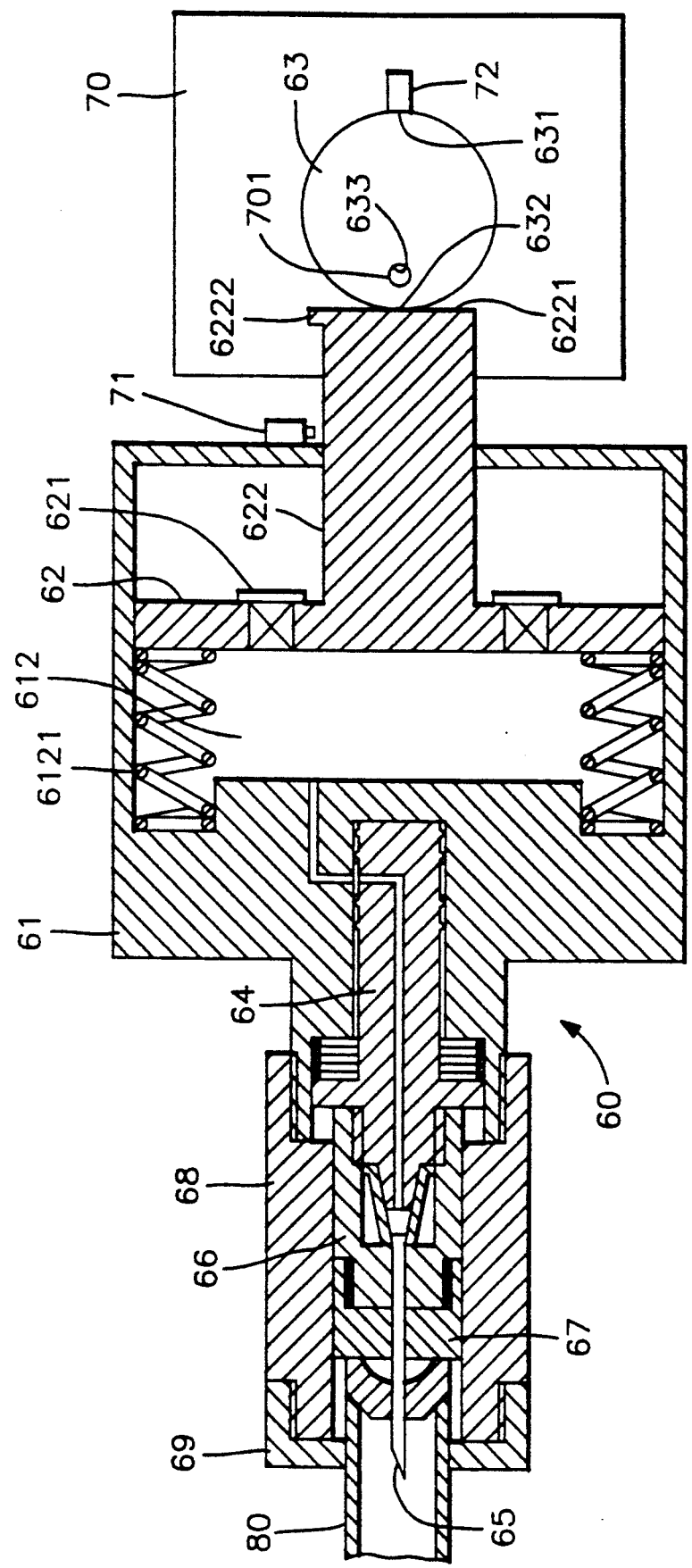
FIG. 6 shows a section view of the second embodiment of the present invention, in the form of the pressure-reducing device, wherein a reciprocating spring of the pressure-reducing transformer extends to press a piston and pushes the piston rod to press and contact a turn-on button, a piston rod end extends to the lateral edge of an eccentric wheel nearby a shaft hole, and a motor and the eccentric wheel are shown in a top view.
Figure 7:
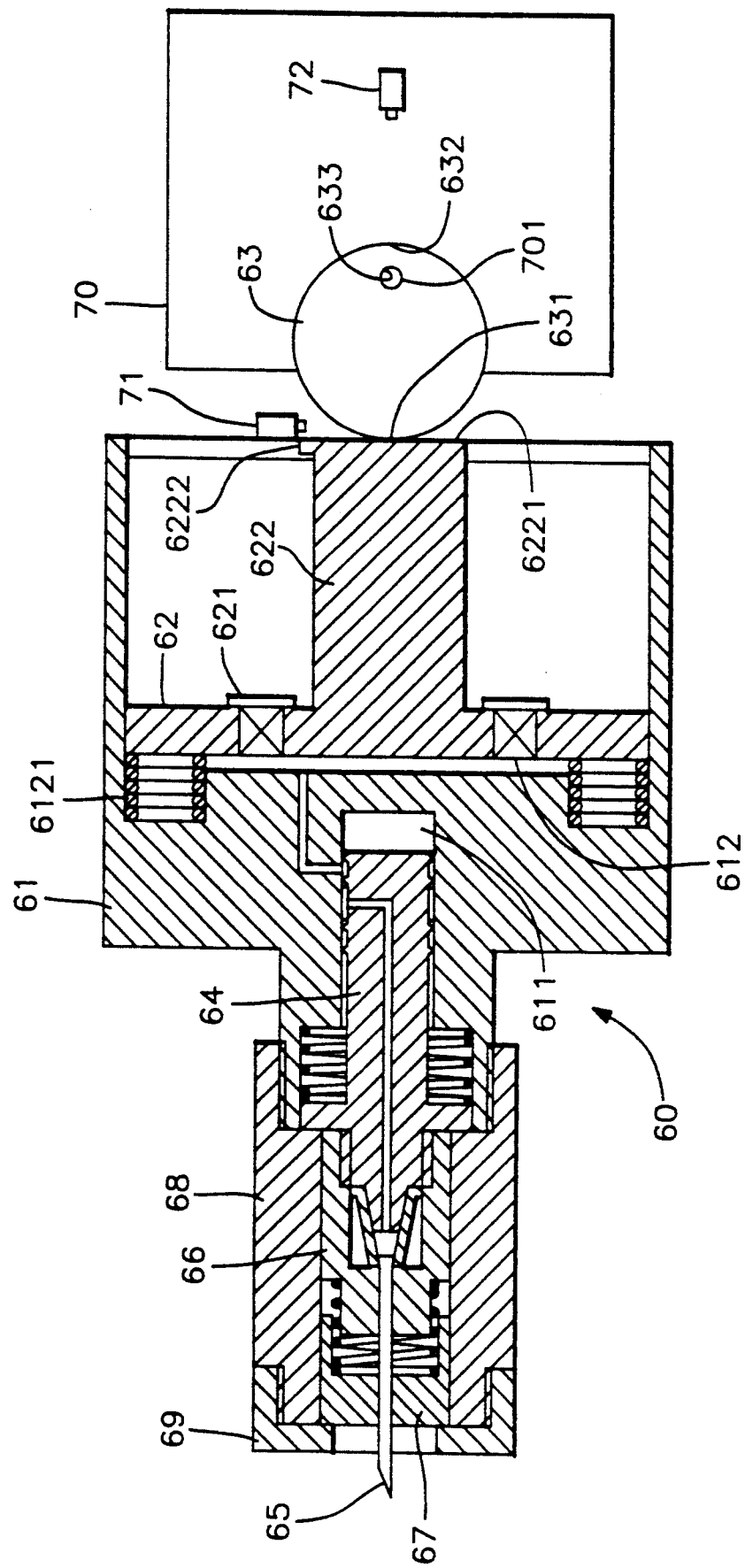
FIG. 7 shows another section view of the second embodiment of the present invention, in the form of the pressure-reducing device, wherein the lateral edge of eccentric wheel far away from the shaft hole presses the piston rod into the pump vacuum chamber so that the piston presses the air out of the pump vacuum chamber, and the motor and eccentric wheel are shown in the top view.
Figure 8:
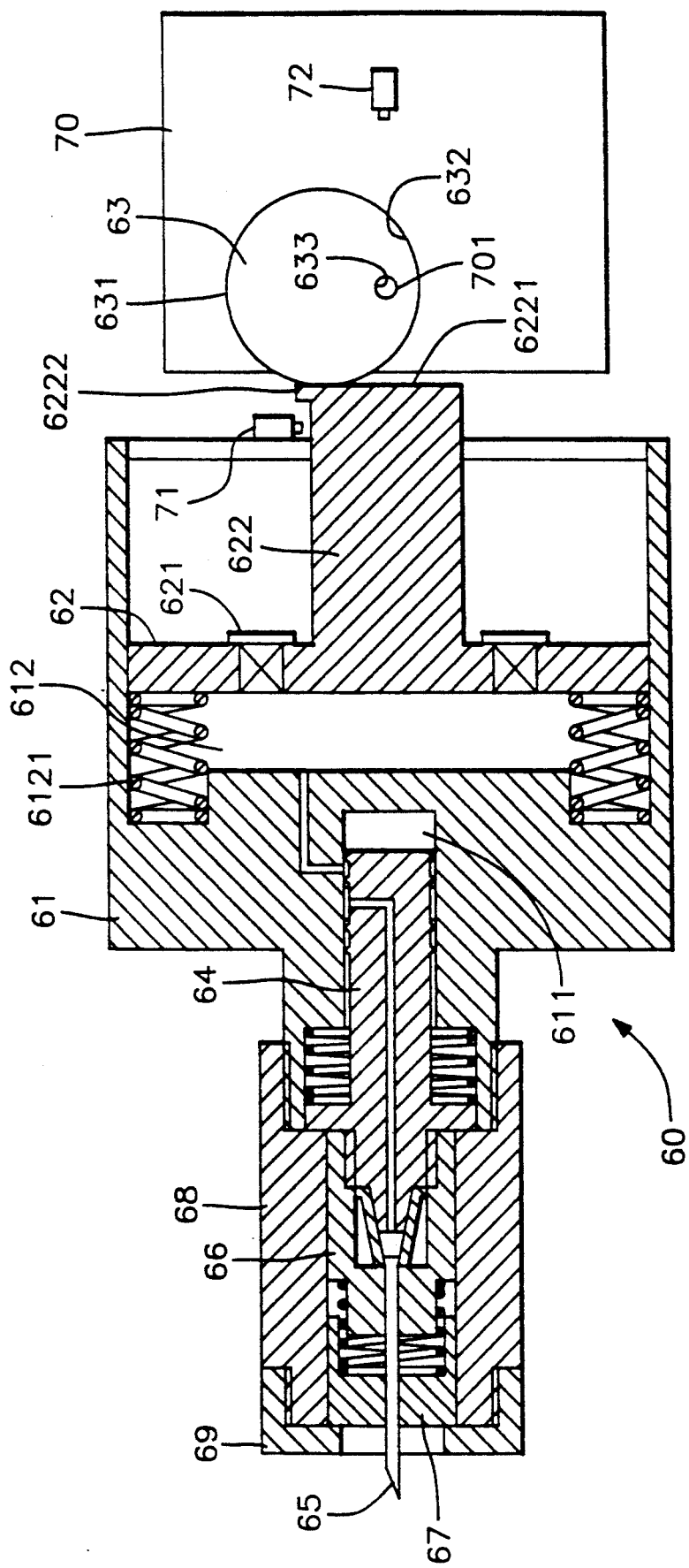
FIG. 8 shows further section view of the second embodiment of the present invention in the form of the pressure-reducing device, wherein the piston which presses the air out of the pump vacuum chamber is reversely pressed by the reciprocating spring and slightly withdraws from the pump vacuum chamber so that the interior of pump vacuum chamber is pressure-reduced to be a vacuum, and the motor and eccentric wheel are shown in the top view.

As shown in FIG. 6 to 8, the overall function of a pressure-reducing device 60 of another shape of present invention is the same as that of the pressure-reducing device 40 of the first embodiment. The pressure-reducing device 60 comprises a vacuum body 61, a piston 62, an eccentric wheel 63, a sliding socket pipe 64, a needle head 65, a needle jacket 66, a sliding sleeve 67, a needle head casing 68 and a sliding sleeve cover 69, wherein the members and functions of sliding socket pipe 64, needle head 65, needle jacket 66, sliding sleeve 67, needle head casing 68 and sliding sleeve cover 69 are the same as those of the pressure-reducing device 40 of the first embodiment, and a blood-gathering tube 80 is the same as the blood-gathering tube 30 of the first embodiment in the aspects of structure and instant pressure-reducing process.

A T-shaped groove 611 and a pump vacuum chamber 612 are provided in the vacuum body 61 of pressure-reducing device 60. A reciprocating spring 6121 and the piston 62 are provided in the pump vacuum chamber 612. Two check valves 621 on the piston 62 can squeeze out the air in the pump vacuum chamber 612 and prevent the air outside the piston 62 from entering into the pump vacuum chamber 612. The piston 62 is externally connected to a piston rod 622. The side edge of end 6221 of piston rod 622 is provided with a protrusion 6222. The eccentric wheel 63 is provided nearby the pump vacuum chamber 612. A shaft hole 633 of the eccentric wheel 63 is connected to a drive shaft 701 of a motor 70. A turn-on button 71 of the motor 70 is provided on the straight route of protrusion 6222 of piston rod 622. A turn-off button 72 of the motor 70 is provided on the revolving route of side edge 631 of eccentric wheel 63.

When too much air is inhaled into the pump vacuum chamber 612 to result in an inadequate vacuum extent, the reciprocating spring 6121 is released from the pressure to extend and press the piston 62, so the piston rod 622 withdraws toward the outside of pump vacuum chamber 612. Before the end 6221 of piston rod 622 contacts a side edge 632 of the eccentric wheel 63, the protrusion 6222 of piston rod 622 contacts and presses the turn-on button 71 of motor 70 to rotate the motor 70 and actuate the revolution of eccentric wheel 63. The revolution of side edge 631 of eccentric wheel 63 which is farer from a shaft hole 633 presses the end 6221 of piston rod 622 to let the piston 62 enter into the pump vacuum chamber 612 and squeeze out the air in the pump vacuum chamber 612 from the check valve 621 on the piston 62. The side edge 631 of eccentric wheel 63 continues revolving and contacts and presses a turn-off button 72 of the motor 70 to turn off the power source. The motor 70 and eccentric wheel 63 stop rotating. As shown in FIG. 8, the side edge 632 of eccentric wheel 63 which is closer to the shaft hole 633 aligns with the direction of piston rod 622. The pressure applied to the piston rod 622 is released. The reciprocating spring 6121 in the pump vacuum chamber 612 properly extends and reversely presses the piston 62 to let the piston 62 and piston rod 622 slightly withdraw outward. The space of pump vacuum chamber 612 is suitably pressure-reduced to be in a state of vacuum and ready for use.

The structure of vacuum body 61 of foregoing pressure-reducing device 60 of the second embodiment is different from that of the vacuum body 41 of pressure-reducing device 40 of the first embodiment, but both of them can automatically maintain the vacuum chamber 412 or the pump vacuum chamber 612 in a state of vacuum with enough low pressure, so their functions are the same.

Third Embodiment

Figure 9:
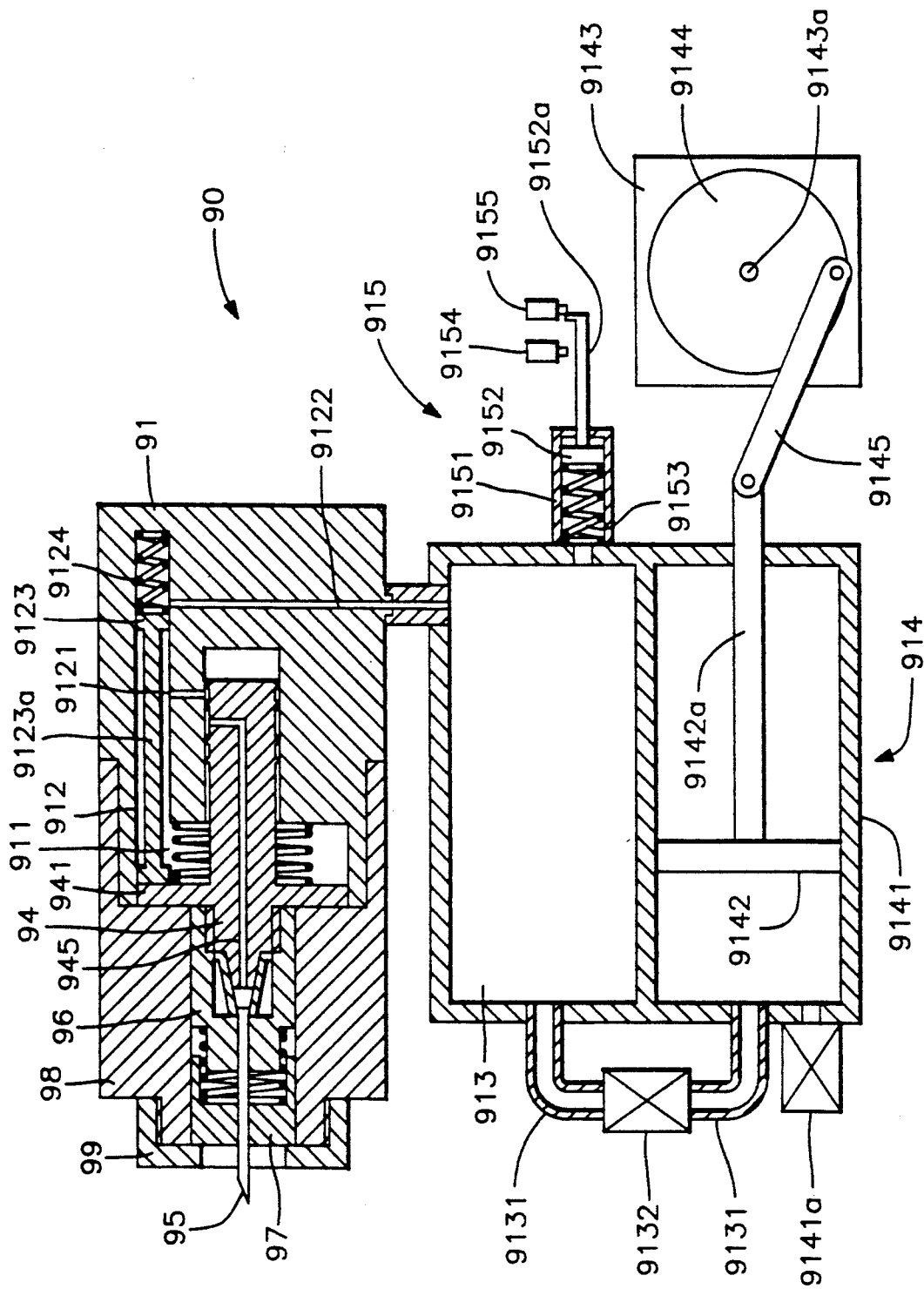
FIG. 9 shows a section view of the third embodiment of the present invention, in the form of the pressure-reducing device, wherein a motor, a drive wheel and a connecting rod are shown in a top view.
Figure 10:
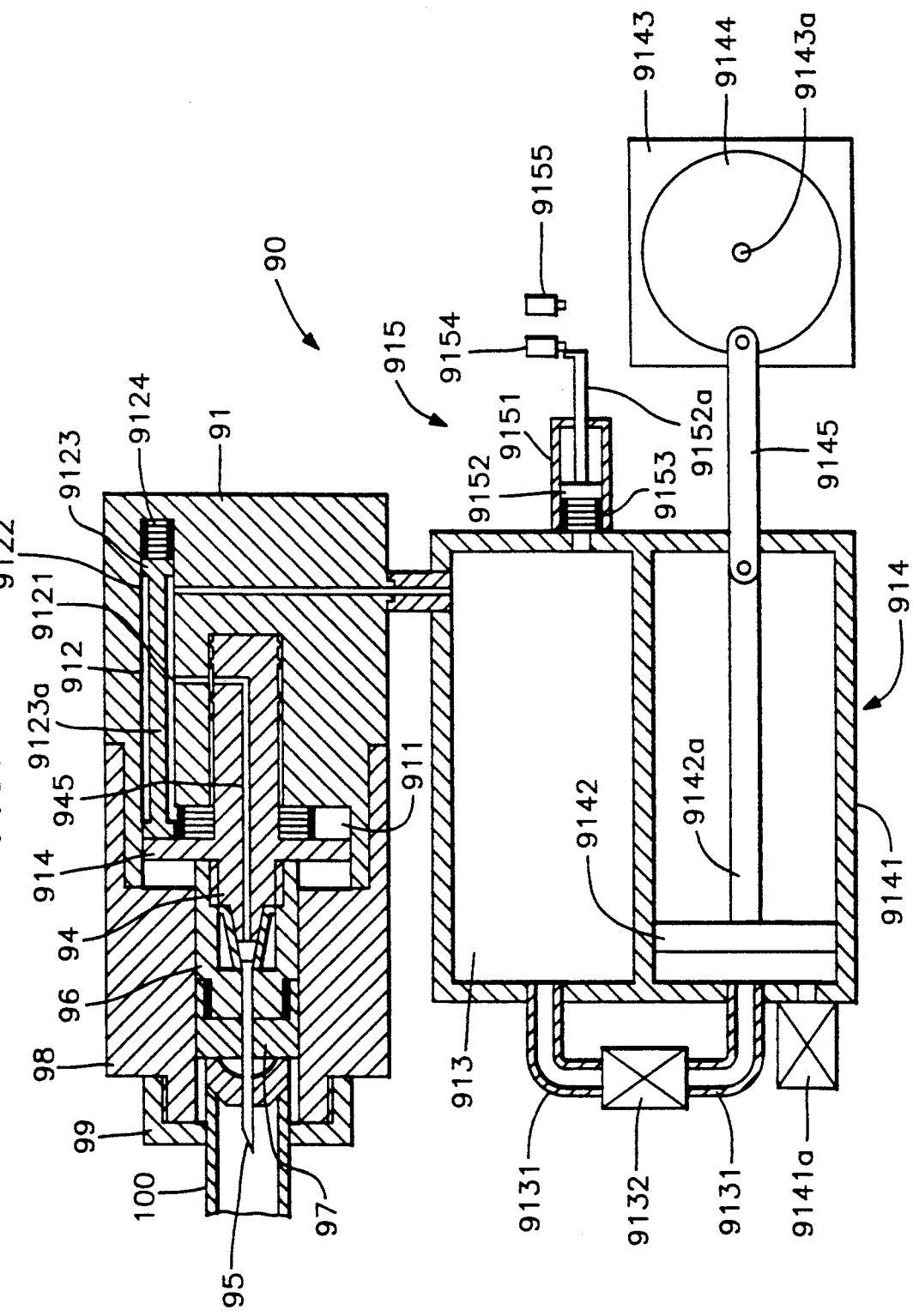
FIG. 10 shows a section view of the third embodiment of the present invention in proceeding with pressure-reducing by a blood-gathering tube being nested into the pressure-reducing device, wherein the motor, drive wheel and connecting rod are shown in the top view.
Figure 11:
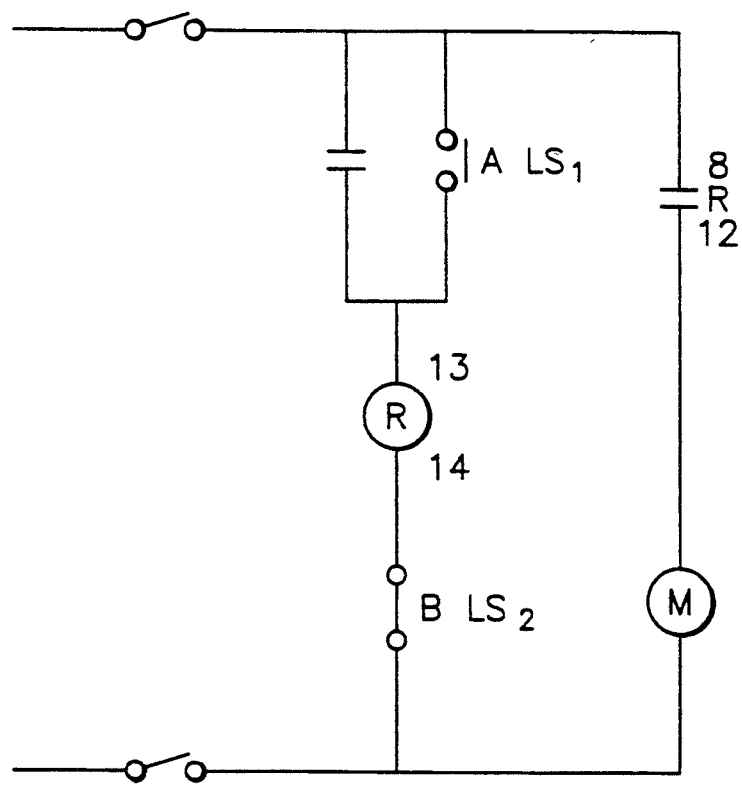
FIG. 11 shows a route view of the second and third embodiment of the present invention, in the form of a motor and a switch of the pressure-reducing device.

As shown in FIG. 9 and 10, it is another form of a pressure-reducing device 90 of the present invention. Its overall function is the same as that of the pressure-reducing devices 40 and 60 of the first or second embodiment. The pressure-reducing device 90 consists of a vacuum body 91, a sliding socket pipe 94, a needle head 95, a needle jacket 96, a sliding sleeve 97, a needle head casing 98 and a sliding sleeve cover 99, wherein the structures of sliding socket pipe 94, needle head 95, needle jacket 96, sliding sleeve 97, needle head casing 98 and sliding sleeve cover 99 are the same as the structures and functions of pressure-reducing devices 40 or 60 of the first and second embodiments. The structure of blood-gathering tube 100 and instant pressure-reducing process are the same as those of the blood-gathering tube 30 or 80 of the first or second embodiment.

A T-shaped groove 911, a piston valve cylinder 912, a vacuum chamber 913 and a piston pump 914 are provided in the vacuum body 91 of pressure-reducing device 90, wherein the piston valve cylinder 912 is provided on one side of the T-shaped groove 911. An air pipe 9121 is provided between the piston valve cylinder 912 and the T-shaped groove 911 to communicate with each other. An air pipe 9122 is likely provided between the piston valve cylinder 912 and vacuum chamber 913 to communicate with each other. A piston 9123 is provided in the piston valve cylinder 912. A reciprocating spring 9124 is provided on one side of the piston 9123. Another side of the piston 9123 is a protruding annulation 941 of the sliding socket pipe 94. When the piston rod 9123a is not pressed by the protruding annulation 941 of sliding socket pipe 94, a shown in FIG. 9, the piston 9123 under the action of extension of a reciprocating spring 9124 is positioned between the opening of air pipe 9121 and air pipe 9122. When the piston 9123a is pressed by the protruding annulation 941 of sliding socket pipe 94, as shown in FIG. 10, the piston 9123 presses the reciprocating spring 9124 and moves toward the reciprocating spring 9124 and slides through the opening of air pipe 9122 to let the air pipe 9121 and air pipe 9122 communicate with each other through the passage of piston valve cylinder 912 so that the air in the blood-gathering tube 100 can be inhaled into the vacuum chamber 913 through the needle head 95, and air groove 945 of the sliding socket pipe 94, the air pipe 9121, piston valve cylinder 912 and air pipe 9122. The blood-gathering tube 100 can be instantly pressure-reduced to be in a state of vacuum and ready for use.

The piston pump 914 is provided on one side of the vacuum chamber 913. An air pipe 9131 is provided between the vacuum chamber 913 and piston pump 914. The air pipe 9131 is provided with a check valve 9132 which makes the air in the vacuum chamber 913 flow into the piston pump 914 in one-way direction. Another side of the vacuum chamber 913 is provided with a piston pressure switch 915. The piston pressure switch 915 consists of a pump 9151, a piston 9152, a spring 9153, a turn-off button 9154 and a turn-on button 9155. The pump 9151 is connected to the vacuum chamber 913. The piston 9152 is provided in the pump 9151. The spring 9153 is provided on the inner side of piston 9152. A piston rod 9152a is provided on the outer side of piston 9152. The turn-off button 9154 and turn-on button 9155 are respectively on the route of piston rod 9152a nearby the outer side of pump 9151. The turn-off button 9154 is closer to the pump 9151 than the turn-on button 9155. When the interior of vacuum chamber 913 is in a state of low pressure of high-degree vacuum, the piston 9152 compresses the spring 9153 on the inner side of pump 9151 under the action of atmosphere pressure on the outer side of pump 9151 to move toward the inside of pump 9151 (i.e. the direction of vacuum chamber 913). when the interior of vacuum chamber 913 is gradually in a state of low-degree vacuum (rising pressure), the pressure of inner and outer sides of piston 9152 gradually tends to be balanced. The spring 9153 is gradually released from pressure and extends to press the piston 9152 to move toward the outer side of pump 9151 (i.e. the direction opposite to the vacuum chamber 913) until the end of piston rod 9152a outside the piston 9152 contacts and presses the turn-on button 9155 to start up a motor 9143 of the piston pump 914. The piston pump 914 consists of a pump 9141, a piston 9142, the motor 9143 and a drive wheel 9144. One wall of the pump 9141 is provided with a check valve 9141a which can exhaust the air in the pump 9141. The outer side of piston 9142 is connected to a piston rod 9142a. The drive wheel 9144 is provided nearby the outer side of pump 9141. The motor 9143 is connected to the lower side of drive wheel 9144. A connecting rod 9145 is provided between the end of piston rod 9142a and one side edge of the drive wheel 9144 to connect each other. When the motor 9143 is started up, a drive shaft 9143a of the motor 9143 actuates the drive wheel 9144 to continue rotating. The drive wheel 9144 drives the connecting rod 9145 to repeatedly pull and push the piston rod 9142a to move in and out of the pump 9141 which exhausts the air to pressure-reduce and form a state of high-degree vacuum. Through the air pipe 9131 attracting the air in the vacuum chamber 913, the vacuum chamber 913 is pressure-reduced to be in a state of high degree vacuum. The piston 9152 of piston pressure switch 915 compresses the inside spring 9153 under the action of atmosphere pressure on the outer side of pump 9151 to move toward the inside of pump 9151 (i.e. the direction of vacuum chamber 913). The end of piston rod 9152a connected to the outer side of piston 9152 moves toward the inside of pump 9151 (i.e. the direction of vacuum chamber 913) to contact and press the turn-off button 9154, and then cut off the power source and stop rotating the motor 9143 of piston pump 914.

In the third embodiment, if to directly connect the air pipe 9121 and air pipe 9122 between the T-shaped groove 911 and vacuum chamber 913, the piston valve cylinder 912 may be saved and the same purpose can be achieved, and the piston valve cylinder 912 may be replaced with the switch of other form; the function of vacuum body 91 of the third embodiment is the same as that of vacuum body 41 or 61 of the first or second embodiment.

Making use of pressure-reducing device of present invention, the blood-gathering tube can be instantly pressure-reduced to form a state of vacuum before blood-gathering. It is not necessary for the medical personnel to worry about whether the blood-gathering tube has enough low pressure for the blood-gathering from time to time, this is the major advantage of present invention.

Since the blood-gathering tube can be pressure-reduced to form a vacuum of low pressure by making use of the pressure-reducing device a few seconds prior to blood-gathering, it is not necessary to worry about whether the blood-gathering tube can be kept in a vacuum of enough low pressure for a long time. The tube body of blood-gathering tube can be made of plastic or other cheap material so as to lower its cost. This is another advantage of the present invention.

While the present invention has been described substantially with reference to specific embodiments thereof, it will be understood that changes and modifications may be made in the structure described and illustrated without departing from the spirit of present invention or exceeding the scope of claims.

I claim:

1. A blood-gathering tube and a pressure-reducing device, wherein said blood-gathering tube comprising a tube body and an elastic cork, a first end of said tube body being open and a second end being closed, a radially central part of said elastic cork being thinner than the periphery of said elastic cork to facilitate penetration by a needle, said elastic cork being tightly nested into said first end of said tube body so as to hermetically seal the interior of said tube body from the exterior, and wherein said pressure-reducing device comprises:

a vacuum body having a vacuum chamber maintained at a low pressure, said vacuum body having an air pipe connected to the interior of said vacuum chamber;

a vacuum pump connected to said vacuum chamber, for maintaining the low pressure in said vacuum chamber;

a sliding socket pipe disposed at least partially in said vacuum body for relative movement with respect thereto, said sliding socket pipe having an internal air passage which can be selectively aligned with said air pipe in said vacuum body;

a hollow needle mounted to said sliding socket pipe, said hollow needle having a central air passage which communicates with the internal air passage of the sliding socket pipe, said hollow needle being capable of piercing said elastic cork when said elastic cork is forced against said needle, wherein penetration of said needle past said elastic cork results in communication between the inside of said hollow needle and the interior of said tube body, and wherein alignment of said internal air passage with the elastic cork, results in the reduction of pressure in the tube body, to the low pressure in the vacuum chamber.

2. A blood-gathering tube and a pressure-reducing device as claimed in claim 1, wherein said pressure-reducing device further comprises a pressure switch responsive to pressure in the vacuum chamber and connected to the vacuum pump so as to activate the pump whenever the pressure inside said vacuum chamber reaches a predetermined upper threshold.

3. A blood-gathering tube and a pressure-reducing device as claimed in claim 1, wherein said hollow needle includes a seat sleeve at the base of the hollow needle, and wherein said hollow needle is removably mounted to said sliding socket pipe by said seat sleeve and a needle jacket, said needle jacket being removably connected to said sliding socket pipe and being disposed circumferentially around said hollow needle and the seat sleeve thereof to thereby secure said hollow needle to the sliding socket pipe in a removable manner.

4. A blood-gathering tube and a pressure-reducing device as claimed in claim 3, wherein said pressure reducing device further comprises resilient means for biasing said sliding socket pipe to a position at which the internal air passage in the sliding socket pipe is not aligned with the air pipe of the vacuum body, said resilient means being yieldable to a sliding force exerted on said sliding socket pipe so that said sliding socket pipe can be displaced relative to said vacuum body to thereby align said internal air passage in the sliding socket pipe with the air pipe in the vacuum body.

5. A blood-gathering tube and a pressure-reducing device as claimed in claim 4, wherein said vacuum body further comprises a T-shaped tubular passage connected to said air pipe in the vacuum body, said tubular passage having a first diameter near and at the air pipe and a second, larger diameter toward the outside of said vacuum body, a ledge being defined at the transition between said first diameter and said second diameter, and wherein said resilient means comprises a coil spring disposed circumferentially around said sliding socket pipe, said sliding socket pipe being received in said T-shaped tubular passage and having an external diameter which corresponds to said first diameter, said sliding socket pipe further comprising a ring disposed circumferentially about said sliding socket pipe, said coil spring being disposed between said ring and said ledge, said ring being located longitudinally on the sliding socket pipe such that said ring completely compresses said coil spring against said ledge when the internal air passage of the sliding socket pipe is aligned with the air pipe in the vacuum body thus preventing further insertion of the sliding socket pipe.

6. A blood-gathering tube and a pressure-reducing device as claimed in claim 3, wherein said seat sleeve has a conical shape, and wherein said sliding socket pipe further comprises a conical needle seat to which said seat sleeve is mounted using the needle jacket.

7. A blood-gathering tube and a pressure-reducing device as claimed in claim 3, wherein said needle jacket comprises:
 a seat sleeve cover having a first external diameter and a first internal diameter, said first internal diameter being large enough to receive the seat sleeve of the hollow needle; and
 a needle head pipe having a smaller internal diameter than said first internal diameter, said smaller internal diameter being large enough for said hollow needle to pass through and extend beyond the needle head pipe, an external ledge being defined around said needle jacket by the transition from said seat sleeve cover to said needle head pipe.

8. A blood-gathering tube and a pressure-reducing device as claimed in claim 7, wherein said pressure-reducing device further comprises:
 a tubular needle casing connected to said vacuum body, said tubular needle casing being arranged concentrically around said hollow needle, said needle jacket, and at least a portion of said sliding socket pipe, said tubular needle casing having an internal diameter at least as large as the diameter of the tube body so that the tube body can be inserted into the tubular needle casing for piecing of the elastic cork using the hollow needle;
 a sliding sleeve disposed around said needle and within said tubular needle casing for sliding movement within said tubular needle casing; and
 a coil spring disposed between said external ledge of the needle jacket and said sliding sleeve, for urging said sliding sleeve generally away from the needle jacket.

9. A blood-gathering tube and a pressure-reducing device as claimed in claim 8, wherein said pressure-reducing device further comprises an annular cover connected to the end of the tubular needle casing, which end is opposite from the vacuum body, said annular cover having a smaller internal diameter than that of the tubular needle casing, thereby limiting the sliding action of the sliding sleeve to within said tubular needle casing.

10. A blood-gathering tube and a pressure-reducing device as claimed in claim 9, wherein said annular cover is connected to said tubular needle casing by a threaded connection; said tubular needle casing is connected to said vacuum body by a threaded connection; and said seat sleeve cover of the needle jacket is connected to said sliding socket pipe by a threaded connection.

11. A blood-gathering tube and pressure-reducing device as claimed in claim 1, wherein said tube body is comprised of plastic.

12. A blood-gathering tube and pressure-reducing device as claimed in claim 1, wherein said elastic cork is comprised of rubber.

* * * * *